United States Patent
Garigapati et al.

(10) Patent No.: US 8,765,189 B2
(45) Date of Patent: *Jul. 1, 2014

(54) ORGANOPHOSPHOROUS AND MULTIVALENT METAL COMPOUND COMPOSITIONS AND METHODS

(75) Inventors: Venkat R. Garigapati, Southborough, MA (US); Kevor S. TenHuisen, Boulder, CO (US)

(73) Assignee: Howmedica Osteonic Corp., Mahwah, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/469,806

(22) Filed: May 11, 2012

(65) Prior Publication Data

US 2012/0288446 A1 Nov. 15, 2012

Related U.S. Application Data

(60) Provisional application No. 61/486,064, filed on May 13, 2011.

(51) Int. Cl.
*A61K 47/24* (2006.01)

(52) U.S. Cl.
USPC ............................ 424/602; 514/769

(58) Field of Classification Search
CPC ................................... A61K 47/482
USPC ............................................. 424/602
See application file for complete search history.

(56) References Cited

U.S. PATENT DOCUMENTS

| | | |
|---|---|---|
| 3,899,556 A | 8/1975 | Heide et al. |
| 4,183,915 A | 1/1980 | Gaffar et al. |
| 4,234,972 A | 11/1980 | Hench et al. |
| 4,373,217 A | 2/1983 | Draenert |
| 4,376,168 A | 3/1983 | Takami et al. |
| 4,491,987 A | 1/1985 | Park |
| 4,563,432 A | 1/1986 | Ehlert et al. |
| 4,563,489 A | 1/1986 | Urist |
| 4,596,574 A | 6/1986 | Urist |
| 4,600,546 A | 7/1986 | Grundei |
| 4,610,692 A | 9/1986 | Eitenmuller et al. |
| 4,629,464 A | 12/1986 | Takata et al. |
| 4,634,720 A | 1/1987 | Dorman et al. |
| 4,636,526 A | 1/1987 | Dorman et al. |
| 4,645,503 A | 2/1987 | Lin et al. |
| 4,654,314 A | 3/1987 | Takagi et al. |
| 4,661,536 A | 4/1987 | Dorman et al. |
| 4,672,032 A | 6/1987 | Slavkin et al. |
| 4,693,986 A | 9/1987 | Vit et al. |
| 4,713,076 A | 12/1987 | Draenert |
| 4,737,411 A | 4/1988 | Graves, Jr. et al. |
| 4,777,153 A | 10/1988 | Sonuparlak et al. |
| 4,781,721 A | 11/1988 | Grundei |
| 4,797,282 A | 1/1989 | Wahlig et al. |
| 4,798,585 A | 1/1989 | Inoue et al. |
| 4,839,215 A | 6/1989 | Starling et al. |
| 4,842,603 A | 6/1989 | Draenert |
| 4,846,838 A | 7/1989 | Takai et al. |
| 4,861,733 A | 8/1989 | White |
| 4,869,906 A | 9/1989 | Dingeldein et al. |
| 4,878,914 A | 11/1989 | Miwa et al. |
| RE33,161 E | 2/1990 | Brown et al. |
| 4,911,720 A | 3/1990 | Collier |
| RE33,221 E | 5/1990 | Brown et al. |
| 4,963,145 A | 10/1990 | Takagi et al. |
| 4,965,039 A | 10/1990 | Schuetz |
| 5,011,495 A | 4/1991 | Hollinger |
| 5,017,518 A | 5/1991 | Hirayama et al. |
| 5,030,396 A | 7/1991 | Saita et al. |
| 5,034,352 A | 7/1991 | Vit et al. |
| 5,053,212 A | 10/1991 | Constantz et al. |
| 5,055,307 A | 10/1991 | Tsuru et al. |
| 5,059,388 A | 10/1991 | Kihara et al. |
| 5,064,436 A | 11/1991 | Ogiso et al. |
| 5,089,195 A | 2/1992 | Ichitsuka et al. |
| 5,092,888 A | 3/1992 | Iwamoto et al. |
| 5,106,626 A | 4/1992 | Parsons et al. |
| 5,135,394 A | 8/1992 | Hakamatsuka et al. |
| 5,149,368 A | 9/1992 | Liu et al. |
| 5,152,791 A | 10/1992 | Hakamatsuka et al. |
| 5,171,720 A | 12/1992 | Kawakami |
| 5,207,710 A | 5/1993 | Chu et al. |

(Continued)

FOREIGN PATENT DOCUMENTS

| | | |
|---|---|---|
| DE | 2620890 | 11/1977 |
| DE | 4216496 | 11/1993 |

(Continued)

OTHER PUBLICATIONS

Hua, W. et al. "New Bone Formation in the in vivo Implantation of Biocermaics," Chinese Medical Journal, vol. 105, pp. 753-757 (1992) (5 pages).
Lange, T.A. et al. "Granular Tricalcium Phosphate in Large Cancellous Defects," Annals of Clinical and Laboratory Science, vol. 16, No. 6, pp. 467-472 (1986) (6 pages).
Zheng, Q. et al. "Artificial bone of Porous Tricalcium Phopshate Ceramics and Its Preliminary Clinical Application," Journal of Tongji Medical University, vol. 12, pp. 173-178 (1992) (6 pages).
W. Schneiders et al., "Effect of modification of hydroxyapatite/collagen composites with sodium citrate, phosphoserine, phosphoserine/RGD-peptide and calcium carbonate on bone remodelling," Bone 40 (2007) pp. 1048-1059, Elsevier, Nov. 19, 2006, Dresden, Germany, www.elsevier.com/locate/bone.
A. Reinstorf et al., "Phosphoserine—a convenient compound for modification of calcium phosphate bone cement collagen composites," Journal of Materials Science: Materials in Medicine 15 (2004), pp. 451-455, 2004 Kluwer Academic Publishers, Dresden, Germany.
International Search Report for Application No. PCT/US2009/64135 dated Apr. 2, 2010.

(Continued)

*Primary Examiner* — Jake Vu
(74) *Attorney, Agent, or Firm* — McCracken & Frank LLC

(57) ABSTRACT

Compositions and methods of their use to adhere a variety of materials together are disclosed herein. The compositions include at least multivalent metal compound, an effective amount of a compound that is structurally similar to phosphoserine, and can be mixed with an aqueous solution. The compositions provide adhesive and cohesive strength in both wet and dry environments which exhibit bond strength upon curing with the possible usage as bone cement for bone filler applications.

37 Claims, No Drawings

(56) References Cited

U.S. PATENT DOCUMENTS

| | | | |
|---|---|---|---|
| 5,258,029 | A | 11/1993 | Chu et al. |
| 5,263,985 | A | 11/1993 | Bao et al. |
| 5,279,831 | A | 1/1994 | Constantz et al. |
| 5,306,303 | A | 4/1994 | Lynch |
| 5,318,779 | A | 6/1994 | Hakamatsuka et al. |
| 5,338,356 | A | 8/1994 | Hirano et al. |
| 5,338,772 | A | 8/1994 | Bauer et al. |
| 5,385,887 | A | 1/1995 | Yim et al. |
| 5,398,483 | A | 3/1995 | Smith et al. |
| 5,409,982 | A | 4/1995 | Imura et al. |
| 5,422,340 | A | 6/1995 | Ammann et al. |
| 5,439,951 | A | 8/1995 | Glimcher et al. |
| 5,464,440 | A | 11/1995 | Johansson |
| 5,492,697 | A | 2/1996 | Boyan et al. |
| 5,508,267 | A | 4/1996 | Czernuszka et al. |
| 5,520,923 | A | 5/1996 | Tjia et al. |
| RE35,267 | E | 6/1996 | Tsuru et al. |
| 5,522,893 | A | 6/1996 | Chow et al. |
| 5,522,894 | A | 6/1996 | Draenert |
| 5,525,148 | A | 6/1996 | Chow et al. |
| 5,531,794 | A | 7/1996 | Takagi et al. |
| 5,536,575 | A | 7/1996 | Imura et al. |
| 5,542,973 | A | 8/1996 | Chow et al. |
| 5,545,254 | A | 8/1996 | Chow et al. |
| 5,571,185 | A | 11/1996 | Schug |
| 5,574,075 | A | 11/1996 | Draenert |
| 5,597,897 | A | 1/1997 | Ron et al. |
| 5,626,861 | A | 5/1997 | Laurencin et al. |
| 5,641,502 | A | 6/1997 | Skalla et al. |
| 5,650,108 | A | 7/1997 | Nies et al. |
| 5,681,872 | A | 10/1997 | Erbe |
| 5,695,729 | A | 12/1997 | Chow et al. |
| 5,707,962 | A | 1/1998 | Chen et al. |
| 5,717,006 | A | 2/1998 | Daculsi et al. |
| 5,741,329 | A | 4/1998 | Agrawal et al. |
| 5,766,618 | A | 6/1998 | Laurencin et al. |
| 5,776,193 | A | 7/1998 | Kwan et al. |
| 5,782,971 | A | 7/1998 | Constantz et al. |
| 5,820,632 | A | 10/1998 | Constantz et al. |
| 5,851,670 | A | 12/1998 | Mitoh et al. |
| 5,866,155 | A | 2/1999 | Laurencin et al. |
| 5,897,953 | A | 4/1999 | Ogawa et al. |
| 5,914,121 | A | 6/1999 | Robey et al. |
| 5,914,356 | A | 6/1999 | Erbe |
| 5,922,025 | A | 7/1999 | Hubbard |
| 5,939,388 | A | 8/1999 | Rosen et al. |
| 5,962,427 | A | 10/1999 | Goldstein et al. |
| 5,988,171 | A | 11/1999 | Sohn et al. |
| 6,010,648 | A | 1/2000 | Yamamoto et al. |
| 6,018,095 | A | 1/2000 | Lerch et al. |
| 6,027,744 | A | 2/2000 | Vacanti et al. |
| 6,030,635 | A | 2/2000 | Gertzman et al. |
| 6,048,964 | A | 4/2000 | Lee et al. |
| 6,051,247 | A | 4/2000 | Hench et al. |
| 6,063,117 | A | 5/2000 | Perry |
| 6,077,989 | A | 6/2000 | Kandel et al. |
| 6,080,801 | A | 6/2000 | Draenert et al. |
| 6,110,503 | A | 8/2000 | Rickey et al. |
| 6,118,043 | A | 9/2000 | Nies et al. |
| 6,129,928 | A | 10/2000 | Sarangapani et al. |
| 6,136,029 | A | 10/2000 | Johnson et al. |
| 6,165,486 | A | 12/2000 | Marra et al. |
| 6,180,605 | B1 | 1/2001 | Chen et al. |
| 6,180,606 | B1 | 1/2001 | Chen et al. |
| 6,187,046 | B1 | 2/2001 | Yamamoto et al. |
| 6,187,047 | B1 | 2/2001 | Kwan et al. |
| 6,194,006 | B1 | 2/2001 | Lyons et al. |
| 6,201,065 | B1 | 3/2001 | Pathak et al. |
| 6,203,574 | B1 | 3/2001 | Kawamura |
| 6,210,612 | B1 | 4/2001 | Pickrell et al. |
| 6,235,225 | B1 | 5/2001 | Okada et al. |
| 6,235,665 | B1 | 5/2001 | Pickrell et al. |
| 6,261,322 | B1 | 7/2001 | Despres, III et al. |
| 6,280,478 | B1 | 8/2001 | Richter et al. |
| 6,281,257 | B1 | 8/2001 | Ma et al. |
| 6,287,341 | B1 | 9/2001 | Lee et al. |
| 6,296,667 | B1 | 10/2001 | Johnson et al. |
| 6,306,297 | B1 | 10/2001 | Ichitsuka et al. |
| 6,316,091 | B1 | 11/2001 | Richart et al. |
| 6,325,992 | B1 | 12/2001 | Chow et al. |
| 6,331,312 | B1 | 12/2001 | Lee et al. |
| 6,335,430 | B1 | 1/2002 | Qvist |
| 6,340,648 | B1 | 1/2002 | Imura et al. |
| 6,346,123 | B1 | 2/2002 | McKay |
| 6,350,462 | B1 | 2/2002 | Hakamatsuka et al. |
| 6,358,532 | B2 | 3/2002 | Starling et al. |
| 6,376,573 | B1 | 4/2002 | White et al. |
| 6,395,036 | B1 | 5/2002 | Czernuszka et al. |
| 6,432,437 | B1 | 8/2002 | Hubbard |
| 6,432,919 | B1 | 8/2002 | Wang et al. |
| 6,451,059 | B1 | 9/2002 | Janas et al. |
| 6,458,162 | B1 | 10/2002 | Koblish et al. |
| 6,479,418 | B2 | 11/2002 | Li et al. |
| 6,495,156 | B2 | 12/2002 | Wenz et al. |
| 6,511,510 | B1 | 1/2003 | De Bruijn et al. |
| 6,521,246 | B2 | 2/2003 | Sapieszko et al. |
| 6,524,345 | B1 | 2/2003 | Valimaa et al. |
| 6,527,810 | B2 | 3/2003 | Johnson et al. |
| 6,533,821 | B1 | 3/2003 | Lally |
| 6,540,784 | B2 | 4/2003 | Barlow et al. |
| 6,547,866 | B1 | 4/2003 | Edwards et al. |
| 6,585,992 | B2 | 7/2003 | Pugh et al. |
| 6,589,590 | B2 | 7/2003 | Czernuszka et al. |
| 6,592,787 | B2 | 7/2003 | Pickrell et al. |
| 6,599,515 | B1 | 7/2003 | Delmotte |
| 6,616,742 | B2 | 9/2003 | Lin et al. |
| 6,667,049 | B2 | 12/2003 | Janas et al. |
| 6,670,293 | B2 | 12/2003 | Edwards et al. |
| 6,692,761 | B2 | 2/2004 | Mahmood et al. |
| 6,696,073 | B2 | 2/2004 | Boyce et al. |
| 6,709,744 | B1 | 3/2004 | Day et al. |
| 6,790,233 | B2 | 9/2004 | Brodke et al. |
| 6,793,725 | B2 | 9/2004 | Chow et al. |
| 6,800,245 | B1 | 10/2004 | Erbe et al. |
| 6,808,561 | B2 | 10/2004 | Genge et al. |
| 6,808,585 | B2 | 10/2004 | Boyce et al. |
| 6,863,899 | B2 | 3/2005 | Koblish et al. |
| 6,949,251 | B2 | 9/2005 | Dalal et al. |
| 6,955,716 | B2 | 10/2005 | Xu et al. |
| 6,987,136 | B2 | 1/2006 | Erbe et al. |
| 6,987,170 | B1 | 1/2006 | Silverman et al. |
| 7,018,460 | B2 | 3/2006 | Xu et al. |
| 7,037,304 | B2 | 5/2006 | Lyles et al. |
| 7,045,125 | B2 | 5/2006 | Erbe et al. |
| 7,066,999 | B2 | 6/2006 | Lin et al. |
| 7,081,161 | B2 | 7/2006 | Genge et al. |
| 7,091,260 | B2 | 8/2006 | Kuehn |
| 7,122,057 | B2 | 10/2006 | Beam et al. |
| 7,172,629 | B2 | 2/2007 | McKay |
| 7,238,203 | B2 | 7/2007 | Bagga et al. |
| 7,258,734 | B2 | 8/2007 | Lin et al. |
| 7,258,735 | B2 | 8/2007 | Lin et al. |
| 7,270,705 | B2 | 9/2007 | Lin et al. |
| 7,294,187 | B2 | 11/2007 | Chow et al. |
| 7,303,646 | B2 | 12/2007 | Qvist |
| 7,318,841 | B2 | 1/2008 | Tofighi et al. |
| 7,357,941 | B2 | 4/2008 | Dalal et al. |
| 7,390,498 | B2 | 6/2008 | Dalal et al. |
| 7,407,542 | B2 | 8/2008 | Lemaitre et al. |
| 7,416,602 | B2 | 8/2008 | Murphy et al. |
| 7,473,312 | B2 | 1/2009 | Barralet et al. |
| 7,494,950 | B2 | 2/2009 | Armitage et al. |
| 7,514,248 | B2 | 4/2009 | Gower et al. |
| 7,514,249 | B2 | 4/2009 | Gower et al. |
| 7,527,687 | B2 | 5/2009 | Genge et al. |
| 7,544,496 | B2 | 6/2009 | Gower et al. |
| 7,547,449 | B2 | 6/2009 | Gower et al. |
| 7,575,628 | B2 | 8/2009 | Lu et al. |
| 7,589,133 | B2 | 9/2009 | Pomrink |
| 7,619,016 | B2 | 11/2009 | Dickens et al. |
| 7,628,851 | B2 | 12/2009 | Armitage et al. |
| 7,632,878 | B2 | 12/2009 | Xu et al. |
| 7,648,728 | B2 | 1/2010 | Yamamoto et al. |
| 8,173,149 | B2 | 5/2012 | Dalal et al. |

(56) References Cited

U.S. PATENT DOCUMENTS

| | | |
|---|---|---|
| 8,232,327 B2 | 7/2012 | Garigapati et al. |
| 8,273,803 B2 | 9/2012 | Garigapati et al. |
| 2001/0014667 A1 | 8/2001 | Chen et al. |
| 2001/0051815 A1 | 12/2001 | Esplin |
| 2002/0022885 A1 | 2/2002 | Ochi |
| 2002/0035402 A1 | 3/2002 | De Bruijn et al. |
| 2002/0082694 A1 | 6/2002 | McKay |
| 2002/0114795 A1 | 8/2002 | Thorne et al. |
| 2002/0115742 A1 | 8/2002 | Trieu et al. |
| 2002/0151466 A1 | 10/2002 | Hubbard et al. |
| 2002/0193883 A1 | 12/2002 | Wironen |
| 2003/0009235 A1 | 1/2003 | Manrique et al. |
| 2003/0031698 A1 | 2/2003 | Roeder et al. |
| 2003/0069638 A1 | 4/2003 | Barlow et al. |
| 2003/0152606 A1 | 8/2003 | Gerber |
| 2004/0002770 A1 | 1/2004 | King et al. |
| 2005/0217538 A1 | 10/2005 | Reinstorf et al. |
| 2006/0089646 A1 | 4/2006 | Bonutti |
| 2006/0096504 A1 | 5/2006 | Grover et al. |
| 2006/0263443 A1 | 11/2006 | Chow et al. |
| 2007/0092580 A1 | 4/2007 | Chow et al. |
| 2007/0092856 A1 | 4/2007 | Chow et al. |
| 2007/0221093 A1 | 9/2007 | Erdrich et al. |
| 2008/0009955 A1 | 1/2008 | Shimp et al. |
| 2008/0028992 A1 | 2/2008 | Lee et al. |
| 2008/0069852 A1 | 3/2008 | Shimp et al. |
| 2008/0095817 A1 | 4/2008 | Murphy |
| 2008/0187571 A1 | 8/2008 | Clineff et al. |
| 2008/0188945 A1 | 8/2008 | Boyce et al. |
| 2009/0028949 A1 | 1/2009 | Leonard et al. |
| 2009/0028960 A1 | 1/2009 | Leonard et al. |
| 2009/0158964 A1 | 6/2009 | Insley et al. |
| 2009/0220475 A1 | 9/2009 | Bohner et al. |
| 2009/0258966 A1 | 10/2009 | Hirayama et al. |
| 2010/0120923 A1 | 5/2010 | Stewart et al. |
| 2010/0121459 A1* | 5/2010 | Garigapati et al. ........ 623/23.61 |
| 2010/0129416 A1 | 5/2010 | Murphy et al. |
| 2010/0168798 A1 | 7/2010 | Clineff et al. |
| 2010/0305626 A1 | 12/2010 | Stewart et al. |
| 2011/0150963 A1 | 6/2011 | Clineff et al. |
| 2011/0151027 A1 | 6/2011 | Clineff et al. |
| 2011/0277931 A1 | 11/2011 | Garigapati et al. |
| 2011/0287067 A1 | 11/2011 | Stewart |
| 2012/0237568 A1 | 9/2012 | Murphy et al. |

FOREIGN PATENT DOCUMENTS

| | | |
|---|---|---|
| DE | 29922585 | 7/2000 |
| DE | 10063119 | 8/2001 |
| EP | 0 267 624 | 5/1988 |
| EP | 0 360 244 | 3/1990 |
| EP | 0 987 032 | 3/2000 |
| EP | 1 027 897 | 8/2000 |
| EP | 1 142 597 | 10/2001 |
| GB | 2078696 | 1/1982 |
| GB | 2 323 083 | 9/1998 |
| GB | 2 348 872 | 10/2000 |
| GB | 2354518 | 3/2001 |
| JP | 59101145 | 6/1984 |
| JP | 59131346 | 7/1984 |
| JP | 59171546 | 9/1984 |
| JP | 60142857 | 7/1985 |
| JP | 6141466 | 2/1986 |
| JP | 6145748 | 3/1986 |
| JP | 6168054 | 4/1986 |
| JP | 61127658 | 6/1986 |
| JP | 63046167 | 2/1988 |
| JP | 64-030572 | 2/1989 |
| JP | 1108143 | 4/1989 |
| JP | 1126977 | 5/1989 |
| JP | 1230412 | 9/1989 |
| JP | 3191963 | 8/1991 |
| JP | 364482 | 10/1991 |
| JP | 429630 | 5/1992 |
| JP | 5042168 | 2/1993 |
| JP | 526504 | 4/1993 |
| JP | 5208877 | 8/1993 |
| JP | 566909 | 9/1993 |
| JP | 5237178 | 9/1993 |
| JP | 5305134 | 11/1993 |
| JP | 588687 | 12/1993 |
| JP | 655219 | 7/1994 |
| JP | 6296676 | 10/1994 |
| JP | 6102582 | 12/1994 |
| JP | 07-023994 | 1/1995 |
| JP | 7291759 | 11/1995 |
| JP | 9030988 | 2/1997 |
| JP | 11-276468 | 10/1999 |
| JP | 2000-262608 | 9/2000 |
| JP | 2001-058885 | 3/2001 |
| JP | 3231135 | 9/2001 |
| WO | WO 86/01113 | 2/1986 |
| WO | WO 87/04110 | 7/1987 |
| WO | WO 87/07495 | 12/1987 |
| WO | 9307910 | 4/1993 |
| WO | WO 93/07835 | 4/1993 |
| WO | WO 93/15721 | 8/1993 |
| WO | WO 93/20859 | 10/1993 |
| WO | WO 94/15652 | 7/1994 |
| WO | WO 94/15653 | 7/1994 |
| WO | WO 95/21634 | 8/1995 |
| WO | WO 97/31661 | 9/1997 |
| WO | WO 97/45147 | 12/1997 |
| WO | WO 97/46178 | 12/1997 |
| WO | WO 98/38949 | 9/1998 |
| WO | WO 98/47485 | 10/1998 |
| WO | WO 99/16478 | 4/1999 |
| WO | WO 99/16479 | 4/1999 |
| WO | WO 99/20319 | 4/1999 |
| WO | WO 99/37246 | 7/1999 |
| WO | WO 00/18443 | 4/2000 |
| WO | WO 00/35511 | 6/2000 |
| WO | WO 00/45870 | 8/2000 |
| WO | WO 00/45871 | 8/2000 |
| WO | WO 00/50104 | 8/2000 |
| WO | WO 01/03709 | 1/2001 |
| WO | WO 01/13970 | 3/2001 |
| WO | WO 01/28603 | 4/2001 |
| WO | WO 01/29189 | 4/2001 |
| WO | WO 01/44141 | 6/2001 |
| WO | WO 01/54746 | 8/2001 |
| WO | WO 01/66163 | 9/2001 |
| WO | WO 02/11781 | 2/2002 |
| WO | WO 02/15881 | 2/2002 |

OTHER PUBLICATIONS

Mai et al. "O-phospho-L-serine: A Modulator of Bone Healing in Calciumphosphate Cements" Biomedizinische Technik, vol. 53, Issue 5, p. 229-233 esp. abstract, Oct. 2008.

Ishikawa et al. "Behavior of a Calcium Phosphate Cement in Simulated Blood Plasma in Vitro" Dental Materials, vol. 10, Issue 1, pp. 26-32 esp. abstract, Jan. 1994.

Chow et al. "A Natural Bone Cement—A Laboratory Novelty Led to the Development of Revolutionary New Biomaterials" Journal of Research of the National Institute of Standards and Technology, vol. 106, No. 6, pp. 1029-1033, Nov. 2001.

Fujimura et al. "A bioactive bone cement containing Bis-GMA resin and A-W glass-ceramic as an augmentation graft material on mandibular bone" Clinical Oral Implants Research, vol. 14, Issue 5, pp. 659-667 esp. abstract, Oct. 2003.

Bundy et al. "The Effect of Surface Preparation on Metal/Bone Cement Interfacial Strength" Journal of Biomedical Materials Research, vol. 21, Issue 6, pp. 773-805 esp. abstract, Jun. 1987.

Clarke "Role of Ceramic Implants, Design and Clinical Success With Total Hip Prosthetic Ceramic-to-Ceramic Bearings" Clinical Orthopaedics and Related Research, vol. 282, pp. 19-30 esp. abstract. Sep. 1992.

International Preliminary Report on Patentability for Application No. PCT/US2009/64135 dated May 26, 2011.

International Search Report and Written Opinion, dated Feb. 21, 2012, International Application No. PCT/US2011/060956, Applicant Howmedica Osteonics Corp. (13 pages).

(56) References Cited

OTHER PUBLICATIONS (Vo-Dinh) Nanotechnology in Biology and Medicine, CRC Press (Jan. 24, 2007) [retrieved on Feb. 8, 2012] entire document retrieved from the Internet: <URL:http://books.google.com/books/aboutNanotechnology_in_biology_and_medicine.html?id=t9IPt1Hu6bAC>, (1 page).

Andriano, K.P. et al., "Preliminary in Vivo Studies on the Osteogenic Potential of Bone Morphogenetic Proteins Delivered from an Absorbable Puttylike Polymer Matrix," *J. Biomed. Mater Re (Appl. Biomater.)* 53:36-43 (2000). (8 pages).

Benoit, M.-A. et al., "Antibiotic-Loaded Plaster of Paris Implants Coated With Poly Lactide-co-glycolide as a Controlled Release Delivery System for the Treatment of Bone Infections," *International Orthopaedics* 21(6):403-408 (1997), (6 pages).

Breitbart, A.S. et al., "Tricalcium Phosphate and Osteogenin: A Bioactive Onlay Bone Graft Substitute," *Plastic and Reconstructive Surgery* 96:699-708 (1995). (10 pages).

Bucholz, R.W. et al., "Hydroxyapatite and Tricalcium Phosphate Bone Graft Substitutes," *Orthopedic Clinics of North America* 18:323-334 (1987). (12 pages).

Chow, L.C., "Solubility of Calcium Phosphates," *Monogr Oral Sci. Basel. Karger* 18:94-111 (2001). (18 pages).

Eggli, P.S. et al., "Porous Hydroxyapatite and Tricalcium Phosphate Cylinders with Two Different Pore Size Ranges Implanted in the Cancellous Bone of Rabbits," *Clinical Orthopaedics and Related Research* 232:127-138 (1988). (12 pages).

Gerhart, T.N. et al., "In vitro Characterization and Biomechanical Optimization of a Biodegradable Particulate Composite Bone Cement," *Journal of Biomedical Materials Research* 22:1071-1082 (1988). (12 pages).

Gombotz, W.R. et at., "Stimulation of Bone Healing by Transforming Growth Factor-Beta$_1$ Released from Polymeric or Ceramic Implants," *Journal of Applied Biomaterials* 5(2):141-150 (1994). (10 pages).

Hutmacher, D.W., "Scaffolds in Tissue Engineering Bone and Cartilage," *Biomaterials* 21:2529-2543 (2000), (14 pages).

Laffargue, PH. et at., "Evaluation of Human Recombinant Bone Morphogenetic Protein-2-Loaded Tricalcium Phosphate Implants in Rabbits' Bone Defects," *Bone* 25:55S-58S (1999). (4 pages).

Metsger, D.S. et al., "Histomorphometric Analysis of Tricalcium Phosphate Ceramic Implanted Into Turkeys," *Bone* 14:243-248 (1993). (6 pages).

Nade, S. et at., "Osteogenesis After Bone and Bone Marrow Transplantation," *Clinical Orthopaedics and Related Research* 181:255-263 (1983). (9 pages).

Nery, E.B. et al., "Tissue Response to Biphasic Calcium Phosphate Ceramic With Different Ratios of HA/βTCP in Periodontal Osseous Defects," *Journal of Periodontology* 63:729-735 (1992). (7 pages).

Ohgushi, H. et al., "Marrow Cell Induced Osteogenesis in Porous Hydroxyapatite and Tricalcium Phosphate: A Comparative Histomorphometric Study of Ectopic Bone Formation," *Journal of Biomedical Materials Research* 24:1563-1570 (1990). (8 pages).

Ohura, K. et at., "Healing of Segmental Bone Defects in Rats Induced by a β-TCP-MCPM Cement Combined with rhBMP-2," *Journal of Biomedical Materials Research* 44:168-175 (1999). (7 pages).

Soriano, I. et at., "Formulation of Calcium Phosphates/Poly (d,l-lactide) Blends Containing Gentamicin for Bone Implantation," *Journal of Controlled Release* 68:121-134 (2000). (14 pages).

Tancred, D.C. et at., "A Synthetic Bone Implant Macroscopically Identical to Cancellous Bone," *Biomaterials* 19:2303-2311 (1998). (9 pages).

Thoma, K. et al., "Biodegradable Controlled Release Implants Based on β-Tricalcium Phosphate Ceramic," *European Journal Pharmaceutics and Biopharmaceutics* 38:107-112 (1992). (6 pages).

Uchida, A. et at., "Bone Ingrowth into Three Different Porous Ceramics Implanted into the Tibia of Rats and Rabbits," *Journal of Orthopaedic Research* 3:65-77 (1985). (13 pages).

Uchida, A. et al., "The Use of Ceramics for Bone Replacement," *The Journal of Bone and Joint Surgery* 66-B:269-275 (1984). (7 pages).

Vaccaro, A.R., "The Role of the Osteoconductive Scaffold in Synthetic Bone Graft," *Orthopedics* 25(5):571-578 (2002). (8 pages).

White, E. et al., "Biomaterial Aspects of Interpore-200 Porous Hydroxyapatite," *Dental Clinics of North America* 30(1):49-67 (1986). (19 pages).

Frayssinet, P. et al., "High Compressive Strength Macroporous Calcium Phosphate Ceramics for Bone Repair," http://www.utc.fr/esb/esb98/abs_htm/722.html. Printed on Oct. 22, 2012 (1 page).

* cited by examiner

ORGANOPHOSPHOROUS AND MULTIVALENT METAL COMPOUND COMPOSITIONS AND METHODS

CROSS REFERENCE TO RELATED APPLICATIONS

The present application claims benefit of U.S. Provisional Application No. 61/486,064 filed May 13, 2011, the entire contents of which are incorporated herein by reference.

REFERENCE REGARDING FEDERALLY SPONSORED RESEARCH OR DEVELOPMENT

Not applicable.

SEQUENTIAL LISTING

Not applicable.

BACKGROUND OF THE INVENTION

1. Field of the Invention

Multivalent metal compound and organophosphate compound compositions that are physiologically-well tolerated and that are useful as adhesive and or bone restorative compositions are disclosed herein.

2. Description of the Background of the Invention

Calcium phosphate composites are used as bone substitutes and bone grafts. These calcium phosphate composites tend to form complexes primarily between calcium-based salts through charge interactions. These composites are used as general bone void fillers and generally lack the adhesive strength sufficient to adhere or fix bones together, for example, fractured surfaces. These prior compositions have insufficient chemical interaction between the calcium phosphate composite and the bone surface or other surface materials and lack sufficient strength to be used to attach bone to bone or bone to other materials.

Certain marine species, such as tubeworms and sand castle worms, rely on secreted proteins for adhesion mechanisms ("The tube cement of *Phragmatopoma californica*: a solid foam," Russell J. Stewart, James C. Weaver, Daniel E. Morse and J. Herbert Waite, Journal of Experimental Biology 207, 4727-4734, 2004). These adhesive proteins contain a high amount of phosphoserine relative to other amino acids. It should be noted that phosphoserine is also referred to as O-phosphoserine. This is an alternate name for the same material and in the present description we will use phosphoserine. The specific mechanism of the phosphoserine involvement with the proteins is not understood. However, phosphoserine has been reported by Reinstorf et al. to be responsible for a specific interaction with calcium containing hydroxyapatite (HA) of bone in U.S. Patent Application Publication No. 2005-0217538A1. In this publication, the authors describe calcium phosphate cements and phosphoserine, whereby the phosphoserine is described as aiding compressive strength and is used as a surface area modifier in the bone cement material. When phosphoserine is used in the range from 0.5% to 5% weight of the composition, the resulting compositions do not exhibit appreciable bone adhesion properties.

SUMMARY OF THE DISCLOSURE

One embodiment of the present disclosure is a composition that comprises a mixture of a multivalent metal compound; and a compound of the formula

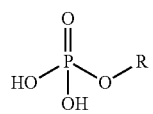

wherein R is one of Groups I, II, III, IV, V, VI, or VII. Group I is

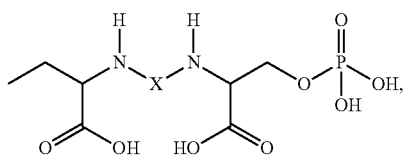

wherein X is selected from the group consisting of Groups Ia, Ib, Ic, Id, and Ie:

Group Ia:

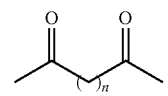

Group Ib:

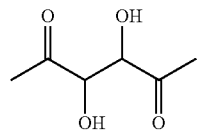

Group Ic:

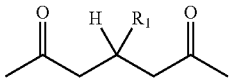

Group Id:

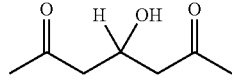

Group Ie:

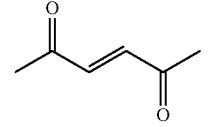

wherein n is an integer from 0 to 6, and $R_1$ is a carboxylic acid group, a sodium carboxylic acid salt or Group If,

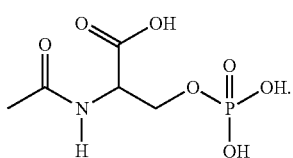

Group II is

[structure: CH3CH2-CH(NH2)-C(=O)-O-R2]

wherein R$_2$ is selected from the group consisting of a pyridoxyl group, a nicotinic acid group, a salicylic acid group, a tyrosine group, and Groups IIa, IIb, IIc, IId, IIe, and IIf:

Group IIa:

[structure: benzyl group -CH2-C6H5]

Group IIb:

[structure: -CH2-C6H4-NO2 (para)]

Group IIc:

[structure: -CH2-C6H4-NH2 (para)]

Group IId:

[structure: -CH2-naphthyl]

Group IIe:

[structure: N-methyl succinimide]

Group IIf:

[structure: -(CH2)n-CH3]

wherein n is an integer from 1 to 11. Group III is

[structure: CH3CH2-CH(NH2)-C(=O)-O-X1-O-C(=O)-CH(NH2)-CH2-O-P(=O)(OH)2]

wherein X$_1$ is a linking group selected from the group consisting of C1 to C12 aliphatic dials, aromatic dials, Group IIIa, sugar, monosaccharides, and disaccharides. Group IIIa is

[structure: -[(CH2)m-O-(CH2)n]y-]

wherein m and n are each integers from 1 to 2 and y is a number from 1 to 100. Group IV is

[structure: HO-C(=O)-CH(CH2CH3)-NH-X2-NH-CH(CH2-O-P(=O)(OH)2)-C(=O)-OH]

wherein the compound comprises a phosphoserine oligomer or a phosphoserine capped polymer of Group IV having from 2 to 10 repeating groups, and wherein X$_2$ is selected from one or more amino acids of Groups IVa, IVb, or IVc, polyesters selected from homopolymers and copolymers of caprolactone, lactide, glycolide, hydroxybutyrate, ethylene glycol linked phosphoserine, and mixtures thereof.

Group IVa:

[structure: CH3-C(=O)-O-[CH2CH2-O]n-C(=O)-CH3]

Group IVb:

[structure: PLGA type polymer with lactide and glycolide units]

Group IVc:

[structure: CH3-C(=O)-(Star Shape PEG)-C(=O)-CH3]

wherein n is a number from 1 to 50, wherein the polylactic glycolic acid (PLGA) of Group IVb has a ratio of lactic acid to glycolic acid being from about 0:100 to about 100:0, more preferably about 30:70 to about 50:50, and the PLGA may be linear, hyperbranched, or star shaped. Group V is

[structure: valine - (CH3)2CH-CH(NH2)-C(=O)-OH]

wherein the compound exists in one of the L, D, and racemic forms. Group VI is

[structure: 4-methylphenylalanine - CH3-C6H4-CH2-CH(NH2)-C(=O)-OH]

wherein the compound exists in one of the L, D, and racemic forms. Group VII is

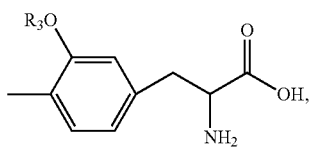

wherein $R_3$ is H or —P(O)(OH)$_2$, and wherein the compound exists in one of the L, D, and racemic forms. The compound is present in an amount from about 10% to about 90% by weight based on the combined weight of the multivalent metal compound and the compound, and the composition further comprises an aqueous medium in an amount of up to about 35% by weight based on the combined weight of the multivalent metal compound, the compound, and the aqueous medium.

A further embodiment of the present disclosure comprises a composition comprising a multivalent metal compound and a compound of Formula VIII or Formula IX. Formula VIII is

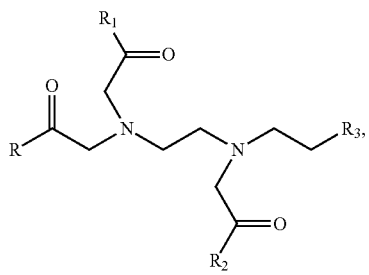

wherein R, $R_1$, $R_2$, and $R_3$ are selected from the group consisting of Group VIIIa or Group VIIIb. Group VIIIa is

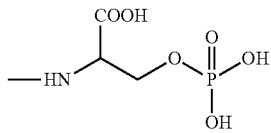

and Group VIIIb is

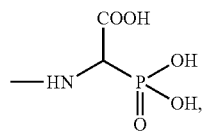

Formula IX is

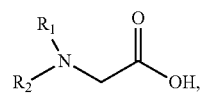

wherein $R_1$ is H or Group IXa and $R_2$ is Group IXa. Group IXa is

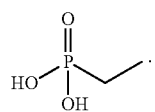

The compound is present in an amount from about 10% to about 90% by weight based on the combined weight of the multivalent metal compound and the compound. The compositions further comprises an aqueous medium in an amount of up to about 35% by weight based on the combined weight of the multivalent metal compound, the compound, and the aqueous medium.

Another embodiment of the present disclosure comprises a kit for forming an adhesive calcium phosphate bone restorative product comprising a composition comprising an effective amount of multivalent metal compound and a compound of any of the above formulas wherein the compound is present in an amount from about 10% to about 90% by weight based on the combined weight of the multivalent metal compound and the compound contained within a first container, and an aqueous medium within a second container. The amount of aqueous medium is up to about 35% by weight based on the combined weight of the multivalent metal compound, the compound, and the aqueous medium.

A further embodiment of the present disclosure comprises a method of repairing a hard surface comprising the steps of mixing a composition comprising an effective amount of a multivalent metal compound and a compound of any of the above formulas wherein the compound is present in an amount from about 10% to about 90% by weight based on the combined weight of the multivalent metal compound and the compound, with sufficient aqueous medium to create a mixture; applying the mixture to the hard surface to be repaired; and allowing the mixture to cure.

An additional embodiment of the present disclosure comprises a method of repairing a bone structure that comprises the steps of applying a composition comprising an effective amount of a multivalent metal compound and a compound of any of the above formulas wherein the compound is present in an amount from about 10% to about 90% by weight based on the combined weight of the multivalent metal compound and the compound directly to the bone structure to be repaired; and allowing the composition to harden by combining in situ with aqueous based bodily fluids.

Still another embodiment of the present invention comprises a method of adhering an implant to bone comprising the steps of applying a composition comprising an effective amount of a multivalent metal compound and any of the above phosphoserine type compounds wherein the phosphoserine type compound is present in an amount from about 10% to about 90% by weight based on the combined weight of the multivalent metal compound and the phosphoserine type compound to at least one surface of the implant; placing the implant into the bone structure; and allowing the composition to harden in situ.

Still another embodiment of the present invention comprises a method of adhering another material to bone comprising the steps of mixing a composition comprising an effective amount of multivalent metal compound and any of the above phosphoserine type compounds, wherein the compound is present in an amount from about 10% to about 90% by weight based on the combined weight of the multivalent metal compound and the compound, with sufficient aqueous medium to create a mixture; applying the mixture to a surface of the bone; placing the surface of the bone into contact with a material to be joined to the bone; and allowing the composition to cure.

Other aspects and advantages of the present disclosure will become apparent upon consideration of the following detailed description.

DETAILED DESCRIPTION OF THE PREFERRED EMBODIMENTS

Multivalent metal compounds such as calcium phosphates, including tetracalcium phosphate (TTCP), react with organophosphate compounds such as amino acid phosphate compounds like phosphoserine to form cements in the presence of aqueous environments that have cohesive and adhesive properties.

Certain amino acid phosphate compounds, such as phosphoserine, have a phosphate group ($PO_4$), a carboxyl group (COOH), and an amine group ($NH_2$) which are all capable of forming ionic interactions with the available metal ions. For rapid and abundant interactions, TTCP is the ideal metal ion source since it has the highest calcium to phosphate ratio (2:1) of the known calcium phosphate compounds and is well tolerated by the body. Basic TTCP is a calcium rich compound that is highly strained and dynamic and metastable in the presence of moisture. In an aqueous environment, the TTCP undergoes a dissolution reaction to release the calcium ions for ionic bonding. This reaction becomes more rapid as the environment becomes more acidic. When it releases the calcium, the phosphoryl oxygen of the phosphate group of the TTCP reactant is available for additional calcium ionic bonding. On this basis the authors hypothesize one method is to manufacture a calcium rich molecule with a calcium to phosphate ratio higher then 2:1 which is even more reactive compared to TTCP. In addition, compositions with less reactivity can also be suitable for use. Such compositions could utilize calcium phosphate compounds with a calcium to phosphate ratio less than 2:1, such as alpha-tricalcium phosphate (1.5:1) or compositions could utilize calcium based compounds which are not from the calcium-phosphate family, such as calcium chloride or calcium oxide. It is preferred that the multivalent metal compound be non-toxic as many uses of these compositions are for medical and/or veterinary uses. However, if the cement is not to be used relative to living organisms, toxicity is of less concern. Suitable multivalent metal compounds include a combination of cations and anions, with examples of suitable cations being; calcium, magnesium, barium, strontium, iron, zinc, titanium, zirconium and mixtures thereof and anions being; phosphates, oxides, carbonates, bicarbonates, sulfates, hydroxides, chlorides, acetates, fatty acid salts, acetylacetones, and nitrates and mixtures thereof. In one embodiment, to obtain a reactive material having cohesive type properties, such multivalent metal compounds include cations such as calcium, strontium and magnesium with anions such phosphates, oxides, hydroxides and chlorides.

It has further been found that certain multivalent metal compound cements that include a certain minimum amount of a wide variety of phosphoserine type compounds and analogs. These compounds will be described in more detail below but the compounds all include the basic phosphoserine structure.

One class of phosphoserine type compounds includes a compound of the formula:

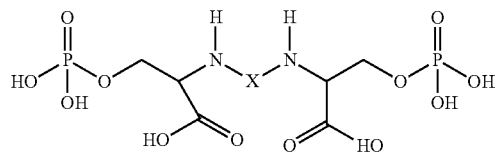

wherein X is selected from the group consisting of ethylene glycol, di-, tri-, tetra- and polyethylene glycol and the following linkers:

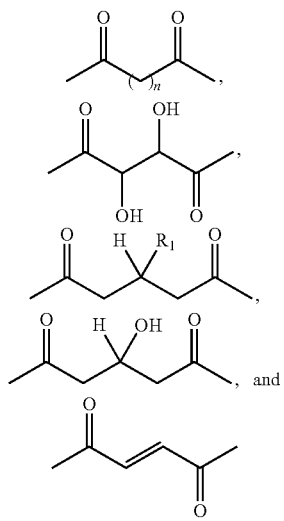

wherein n is an integer from 0 to 6, $R_1$ is a carboxylic acid group, a sodium carboxylic acid salt or

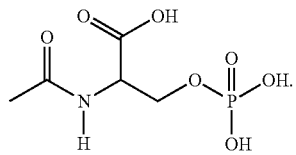

One possibility is the synthesis of nitrogen-linked O-phospho-L-serine (OPLS) analogs, of which, there are a number of synthesis the methods, one of which involves the dissolution of succinic acid (10 mmol) in water (20 ml) and cooled either by refrigerator or, say, in an ice bath to temperatures above freezing (~5° C.). To this solution, 25 mmol of N-(3-Dimethylaminopropyl)-N'-ethylcarbodiimide hydrochloride (EDC) and 50 ml of triethylamine is added. The mixture is then continually stirred for about 5 minutes, followed by the addition of phosphoserine (10 mmol). The reaction mixture is stirred for a period of time at room temperature to allow for the reaction to take place. The mixture is then extracted with dichloromethane and the solvent removed. The residue is then dried under vacuum for a period of time until sufficiently dried (<1% moisture). The material can be used directly in the formulations listed above as an organophosphorous base line compound.

A second class of phosphoserine type compounds includes a compound of the formula:

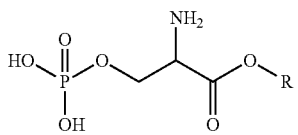

wherein R is one of the following:

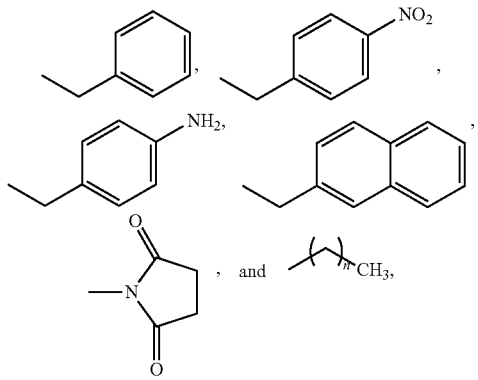

a pyridoxyl group, a nicotinic acid group, a salicylic acid group, and a tyrosine group, wherein n is an integer from 1 to 11.

A third class of phosphoserine type compounds includes a compound of the formula

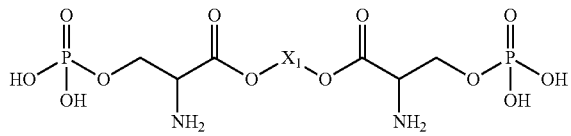

wherein $X_1$ is a linking group selected from the group consisting of C1 to C12 aliphatic diols, aromatic diols,

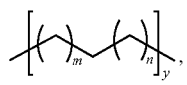

sugar, monosaccharides and disaccharides, wherein m and n are each integers from 1 to 2 and y is a number from 1 to 100.

A fourth class of phosphoserine type compounds includes a phosphoserine oligomer or a phosphoserine capped polymer of the formula:

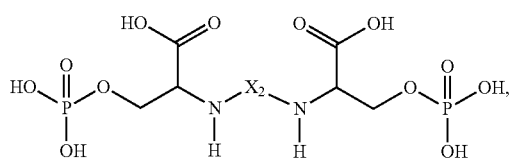

having from 2 to 10 repeating groups and wherein $X_2$ is selected from one or more amino acids, the following linkers:

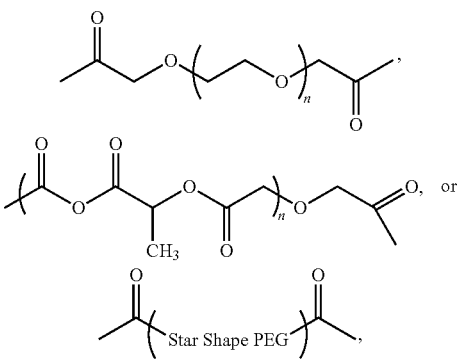

and polyesters selected from homopolymers and copolymers of caprolactone, lactide, glycolide, hydroxybutyrate and mixtures thereof, wherein x is a number from 1 to 50, and wherein the PLGA has a ratio of lactic acid to glycolic acid from about 0:100 to about 100:0, more preferably about 30:70 to about 50:50, and the PLGA is linear, hyperbranched and star shaped.

One possibility is the synthesis of ethylene glycol linked OPLS esters, of which, there are a number of synthesis the methods, one of which involves the addition of ethyleneglycol bisglycidyl ether (10 mmol) to anhydrous dichloromethane, to which 20 mmol of phosphoserine was added, followed by 20 ml of trifluoroacetic acid. This mixture is continually stirred for, say, 30 min. The reaction mixture is then transferred onto a separatory funnel and extracted with water. The aqueous layer is then lyophilized to give a white powder form of ethylene glycol linked OPLS esters.

A fifth class of phosphoserine type compounds includes a compound of the formula

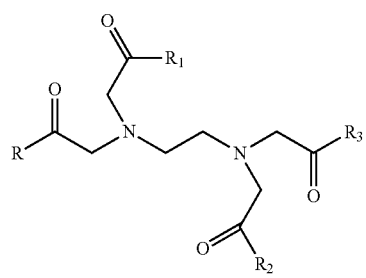

wherein R, $R_1$, $R_2$, and $R_3$ are one of the following:

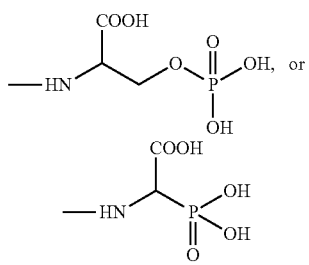

A sixth class of phosphoserine type compounds include formula which exist in the L, D, and racemic form;

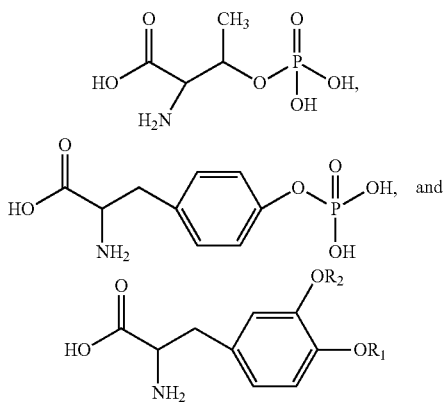

wherein either $R_1$ is —P(O)(OH)$_2$ and $R_2$ is H, forming the compound known as DOPA monophosphate, or $R_1$ and $R_2$ are both —P(O)(OH), forming the compound known as DOPA diphosphate. As noted below the various stereoisomers of these compounds can also be used including the D, the L and the DL forms.

A seventh class of phosphoserine type compounds includes a compound of the formula

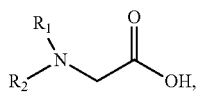

wherein $R_1$ is H or the following group and $R_2$ is the following group:

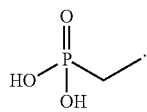

The above DOPA-Phosphates could be synthesized by a number of various methods, one of which would be where 117 ml of Phosphorous oxychloride (POCl$_3$) [1.2 mol], is added to 45 ml of water (2.5 mol). The solution is then stirred for approximately 1 hour at 5° C. This allows for the formation of monochlorophosphate [Cl—P(O)(OH)$_2$]. To this mixture, 25 g of DOPA (0.125 mol) is added and the mixture heated to approximately 60° C. with continuous stirring. The reaction is quenched by drop wise addition of 18 ml of water to degrade the unreacted monochlorophosphate. The reaction mixture is then acidified with 1 Normal HCl. The reaction mixture is kept in a cooled environment, e.g. in a refrigerator, for a period of time to cool the solution down and allow precipitation of DOPA-Phosphates to occur. Once precipitation has occurred, the crystals can be collected and washed with cold water to remove any remaining reactant residues. These crystals can be used directly to formulate as described above.

The compositions as described herein have many unique properties not found in prior calcium phosphate compositions. One particularly important property is that the compositions have a tacky state immediately subsequent to mixing with an aqueous medium. This tacky property is retained for a number of minutes, sometimes up to 12 minutes depending on the application requirement, typically up to about 4 minutes, and preferably up to about 2 minutes, after mixing with the aqueous medium. The time of the tacky state is dependent on a number of factors including relative ratio of the components, the particle sizes of the component materials, the presence of additives and the like. During this time the compositions will adhere bone to bone and bone to other materials, often without the need for external clamping or other application of pressure. The tacky state is not so aggressive that the composition will permanently affix the materials together at this point in time. The materials can be moved relative to each other and also be re-opposed during the tacky state without appreciable loss of ultimate cured strength. This is important in a medical setting so that the user can make sure the bone and the other material to be adhered to the bone are in the proper position relative to each other.

The tacky state is followed by a putty state. In the putty state, the tacky property has substantially disappeared and the compositions can be shaped or sculpted. In addition, during the putty state, the composition can be formed into shapes or used to fill voids in bone in a manner similar to putty. This putty state is retained for a number of minutes, sometimes up to 15 minutes depending on the application requirement, typically up to about 8 minutes, and preferably up to about 5 minutes, after mixing with the aqueous medium. Like the tacky states, the putty state is dependant on a number of factors including the relative ratio of the components, the presence of additives, the particle size of the components and the like.

Because the items to be affixed can be repositioned during the tacky state or the compositions can be shaped during the putty state, this combined time of the tacky state and the putty state is sometimes referred to as the working time. In some embodiments, compositions of the present invention have a working time up to 27 minutes from initial mixing. In other preferred embodiments, compositions have a working time of up to 12 minutes from initial mixing and often the working time is up to about 7 minutes after which time the compositions have sufficiently begun hardening. Further manipulation after the working time will result in degradation of ultimate strength of the bond.

After the putty state, the composition hardens like a cement to form a substantially stable bond between the materials. The bond is made stable initially due to the adhesive properties of the composition. The bond is maintained over time, in vivo, due to bone ingrowth into the composition and materials concurrent with any resorption of the compositions and materials. In the cement state, the composition hardens and the materials that have been affixed to each other cannot be separated without the application of significant force. The compositions typically will begin to harden within about 12 minutes, and often within about 7 minutes, after mixing with the aqueous medium. The amount of time to reach the cement state is also dependant of the same factors listed above.

It should be understood that in certain embodiments of the present invention, for instance in applications in which the composition serves mainly as an adhesive, it is not desirable to work the product through a putty state. For these applications, the composition is optimized to include a tacky state with little or no putty state. In these embodiments, the working time is predominantly the tacky state (and shortened) and can range from up to about 2 minutes to up to about 12 minutes after mixing with an aqueous medium.

A further important property of the compositions is that these compositions have significant coherency and integrity within a wet environment. In the medical field, this would include a surgical site, a wound or similar situation where blood and other bodily fluids are present. The tacky state, the putty state and the cement state are not inhibited by environment. Specifically, all can transpire in either a wet environment or in a dry environment. In order to get the desirable properties, the user need not ensure that the application site is clean and dry. In a wet environment, the compositions tend to remain together and the presence of the liquid does not significantly affect the integrity of the composition or the ultimate strength properties. In certain embodiments in fact, it is preferred that the local aqueous medium (such as blood, bone marrow) be incorporated into the composition.

The compositions as described herein are useful in a wide variety of medical applications. One use of the compositions is to adhere bone fragments together within the body. This is useful, for example, during surgery to allow for temporary fixation prior to definitive hardware placement, and to enhance fracture fixation by adhering both load and non-load bone fragments together alone or in the presence of appropriate immobilization. The compositions may also be used in screw augmentation or bone anchor applications. In some embodiments, the compositions are used to enhance screw or bone anchor fixation into low density cancellous bone at and/or after surgery, to allow screw fixation when the core diameter of the screw hole is larger then the screw major diameter, for instance to reattach screws that have stripped from the surrounding material, to adhere a metal or bioresorbable plate to fractured bones allowing for reduction and/or elimination of metal or bioresorbable screws used to fix plate to bone. The compositions also have the capacity to enhance fixation of a joint replacement prosthesis to bone (e.g. hip acetabular cup or femoral stem). The compositions adhere the junction of at least one of a tendon, ligament, cartilage, a bone graft, and/or dental implants to bone. The compositions may be used to support new bone growth for dental socket or dental ridge augmentation. The compositions have the capacity to adhere to bony defect perimeters while filling gaps creating a seal to prevent leakage (e.g. cerebral spinal fluid). Furthermore, the compositions may also be used in ossicular chain reconstruction to adhere middle ear ossicles together. The adhesive properties of the compositions of the present invention to bone and bone to other materials make them useful to provide bony contour for facial bone augmentation applications. These compositions are also useful for gluing cancellous bones, cortical bones and a combination of both, whether in fatty or greasy environments potentially without any surface pretreatment prior to application.

One particularly useful use of the compositions is as a bone restorative composition. The term "bone restorative composition" includes compositions that are useful to restore and/or repair bone, such as hone adhesives, bone cements, bone glues, bone putties, bone void fillers, bone replacement compositions, cements and/or adhesives to fix screws, implants and at least one of a tendon, ligament, cartilage, a bone graft, and/or a dental implants to bone.

As noted above, the compositions have a tacky state shortly after initial mixing. This tacky state enables two items, such as two pieces of bone, bone and another material or two non-bone materials to be held together by the composition itself, without the need for external force, until the composition sets to the final hardened cement state. The amount of force needed to remove two opposed pieces of material from each other is the separation strength. For the composition as described herein, these compositions have a separation strength during the tacky state within the first 4 minutes and preferably within the first 2 minutes after initial mixing from about 10 kPa to about 250 kPa and preferably from about 50 kPa to about 150 kPa. For certain applications it may be useful to have a longer tacky state whereby certain compositions have a separation strength which continues in this range for up to 12 minutes. This separation strength is sufficiently high that the items to be joined need not be held together unless there is an apposing strength of the items greater than the separation strength and also, the items can still be repositioned or even re-apposed without loss of ultimate bond strength upon curing.

It has been found that in the present compositions the multivalent metal compound, particularly the multivalent metal phosphates, have particularly useful properties when combined with the small molecular amino acid species. Preferred multivalent metal compound phosphates include calcium phosphate, magnesium phosphate, barium phosphates, strontium phosphate, titanium phosphate, zirconium phosphate, and mixtures thereof.

The multivalent metal compound should be present in an amount of the dry ingredients of from about 10% to about 90% on a weight basis. Preferred amounts range from about 40% to about 80% on a weight basis and optimum amounts range from about 55% to about 65% on a weight basis.

A second necessary component of the compositions is a phosphoserine type compound of the type discussed above. These compounds that are structurally similar to phosphoserine, which contain the reactive phosphonate or phosphate, and which have COOH functional groups, are capable of interacting with the multivalent metal cation within the multivalent metal compound to form a multivalent metal-based matrix and are referred to as compounds structurally similar to phosphoserine in this description. The combination of these functional groups plus the geometry such as the chain length between the phosphorous and the COOH are unique aspects to the molecules which affect the level of adhesive bonding strength to substrate surfaces such as bone and metal.

The preferred compounds that are structurally similar to phosphoserine are phosphoserine, tyrosine phosphate and threonine phosphate which may be any form including the D, the L, or the racemic DL form of the compound. The stereochemistry of these compounds does not seem to have any impact on the properties of the compositions disclosed herein.

It has been found that when the quantity of compounds that are structurally similar to phosphoserine is increased beyond about 10% w/w of the combination of the compound and the multivalent metal compound, more generally in the range of about 10% to about 90%, more typically in the range of 15% to about 50%, or preferably from about 20% to about 40%, the tacky and adhesion properties of the resulting compositions were significant. At such levels, the influence of compounds that are structurally similar to phosphoserine extends beyond internal interaction with the cement, but also extends to significant binding with the hydroxyapatite architecture and proteins of bone. At below about 10% by weight of the compound structurally similar to phosphoserine, the compositions do not have a tacky state and these compositions do not have adhesive properties.

Factors that may affect the length of the tacky state, the length of the putty states and the ultimate cure time, as well as strength properties of the compositions include: the percentage (w/w) multivalent metal compound and the compounds that are structurally similar to phosphoserine based solely on the weight of the multivalent metal compound and the compounds that are structurally similar to phosphoserine in the composition, the selection of the compounds that are structurally similar to phosphoserine, the particle size and surface area of the multivalent metal compound, the crystallinity of the multivalent metal compound, the solubility or the multivalent metal compound, and the nature and quantity of any additives and/or fillers which may be combined to the composition to enhance the material properties.

The mean particle size of the multivalent metal compound should be below 1000 μm, preferably 1-250 μm, most preferably 10-100 μm. As the mean particle size of the multivalent metal compound is reduced, the multivalent metal compound tends to dissolve too fast and these compositions may not be practical for all uses as disclosed herein. On the other hand if the multivalent metal compound has a mean particle size of greater than about 1000 μm, the intra-operative performance of the compositions may not have the desired initial strength and be too slow to set. If a longer working time is desired, then multivalent metal compound with a larger mean particle size can be used; however, if a shorter working time is desired, then multivalent metal compound with a smaller mean particle sizes can be used. In certain use environments, compositions that have a multi-modal mean particle size distribution with, for example, one mode less then 50 μm and the other mode above 50 μm can provide unique properties such as a fast initial cure rate from the smaller mean particle size mode combined with higher intrinsic compression strength of the material from the larger mean particle size mode.

The aqueous based mixing media useful for combining the multivalent metal compound and compound that is structurally similar to phosphoserine powders should be present in an amount of up to about 35% on a weight basis of the combined weight of the multivalent metal compound, the compound, and the aqueous medium. In one embodiment, the aqueous based mixing media is present in an amount from about 15% to about 35% by weight based on the combined weight of the multivalent metal compound, the compound, and the aqueous medium. In other embodiments, the aqueous based mixing media is present in an amount from about 20% to about 30% by weight based on the combined weight of the multivalent metal compound, the compound, and the aqueous medium. In a preferred embodiment, the aqueous based mixing media is present in an amount from about 15% to about 30% by weight based on the combined weight of the multivalent metal compound, the compound, and the aqueous medium. Examples of the aqueous liquid include, but is not limited to, water, buffers such as sodium phosphate, saline, isotonic dextrose solution, and blood based products such as whole blood, plasma, platelet rich plasma, serum, and/or bone marrow aspirate, PEG solution, having the PEG molecular weight from 1000 to 20,000 and a concentration from about 0.1% to about 20%. The blood based products are used with the goal of achieving enhanced rate of bone healing and remodeling. It is also possible to use the compositions without premixing with an aqueous medium if the composition is to be used in a sufficiently wet environment that the aqueous medium can be absorbed from the in situ site. In this situation, the composition can be dusted on or other wise applied to the desired site and then mixed with the liquids that are already present at the site.

Additives may enhance the material properties. These properties include the handling, porosity, intrinsic material strength, and bone healing rate (osteogenic). Suitable additives include: alpha or beta tri-calcium phosphate (α-TCP or β-TCP), calcium sulfate, calcium silicate, calcium carbonate, sodium bicarbonate, sodium chloride, potassium chloride glycerol phosphate disodium, amino acids such as serine, excess amounts of phosphoserine, polyols (such as glycerol, mannitol, sorbitol, trehalose, lactose, and sucrose), silk, keratin (primarily found in human hair), autologous bone powder or chips, demineralised bone powder or chips, collagen, various biodegradable polymers such as polyethylene glycol (PEG), polylactic acid (PLA) in the L, D, and racemic forms, polyglycolic acid (PGA), and copolymers of lactic and glycolic acid (PLGA), further including biodegradable block polymers such as poly-L-lactic acid (PLLA)-polyethylene glycol (PEG)-poly-L-lactic acid (PLLA) block polymer, BMP7 (bone morphogenetic protein), stem cells, parathyroid hormone (PTH), bisphosphonates, and mixtures thereof. In addition, other additives and/or fillers could be incorporated which offer surgical visual aids & anti-infective properties.

The α-TCP and β-TCP additive component typically is also in particulate or granular form. The granules presently contemplated have an overall diameter size in the range of about 0.1 to 2 mm, or preferably between 0.5 to about 1 mm, Larger and smaller granules can be used depending on the other components of the composition and the desired end properties. In the present compositions, the particle size of the granules has an impact on the mechanical strengths of the resultant compositions. The total porosity of these granules is in the range of 40-80%, more preferably 65-75%, and the average pore diameter size of the granules in these compositions is in the range of 20-500 μm, preferably 50-125 μm. The granules do not dissolve within the present embodiments during the curing phase, but interact as a solid particle with the other components of the compositions. In the present compositions, the porosity and pore size listed here has an impact on the resorption characteristics of the resultant compositions and to allow for bony in growth and healing as described by Dalal et al. in U.S. Pat. No. 6,949,251.

The additives that affect the porosity include cement curing pore forming agents such as calcium carbonate or sodium bicarbonate, granules with pre-formed pores made from alpha or beta tri-calcium phosphate (α-TCP or β-TCP), biodegradable polymers usually in fiber form that open channels or pores as they degrade relatively quick in vivo such as PGA, or copolymers such as PLGA, or biodegradable fibers that open channels or pores as they degrade over relatively long time periods such as PLLA, silk, keratin, collagen, autologous bone powder or chips, or demineralized bone powder or chips. Other biodegradable polymers in the form of powders, can be used such as PLA in the L, D, and racemic forms, PGA, PLGA, PEG, or block polymers such as PLLA-PEG-PLLA. Small molecules may also be used which leach away relatively quickly from the cement as it cures; these materials may include sodium chloride, potassium chloride, glycerol phosphate disodium, polyols (such as glycerol, mannitol, sorbitol, trehalose, lactose, & sucrose), amino acids such as serine, and/or excess amounts of phosphoserine. Other materials that form pores may dissolve or resorb over time in vivo and release from the cement opening pores; these materials include calcium sulfate, α-TCP or β-TCP powder or granules. Granules can be used to alter the in vivo resorption profile, such as α-TCP or β-TCP granules, or hybrid granules made from calcium sulfate and α-TCP or β-TCP in which the calcium sulfate portion resorbs more quickly.

The additives that affect the bone healing rate driven by new bone ingrowth can be influenced by the level of porosity of the cured cement. This rate can be manipulated by the number of pores and size of the pores created within the cured cement. Achieving such porosity up to 60% v/v was demonstrated by controlling the ratio of composition ingredients. The porosity that develops during the curing process can be controlled by the amount of pore forming agent added (such as calcium carbonate, sodium carbonate, and potassium carbonate), the level of compound structurally similar to phosphoserine added, the level of aqueous solution used, and/or the level of other agents added to the composition. Increasing the porosity reduces the material intrinsic strength; however, a balance of porosity vs. strength is critical for achieving the clinical application. Additives that increase the intrinsic material strength can be incorporated to offset the loss of strength by creating porosity.

The additives that increase the intrinsic material properties, such as strength, toughness, and flexibility, of the cured cement include silk, keratin, collagen, autologous bone powder or chips, demineralized bone powder or chips, calcium silicate, calcium sulfate, biodegradable polymers (such as PLLA, PGA, PLGA) or biodegradable block polymers (such as PLLA-PEG-PLLA), also granules made from calcium sulfate, α-TCP, β-TCP or hybrids thereof. These material additives improve the intrinsic strength or toughness by preventing crack propagation in the cement when under load. These material additives can be supplied as granules, powders or fibers. An important aspect of these fibers is the size. The fiber size can be defined by the aspect ratio (length:diameter). The preferred aspect ratio is from 2:1 to 50:1; more preferable from 10:1 to 30:1. The overall length of the fiber can be up to 5 mm; however, since the material could be used as bone to bone adhesive, the length of the fiber may be more appropriate at lengths up to 2 mm. The additives can be added into the composition up to 30% w/w based on the total weight of the composition to increase the intrinsic strength of the material; however, as such levels the adhesive properties decrease; therefore, a balance between intrinsic strength and material adhesive properties is required.

The additives that act as visual aids in the surgical procedure include colorants such as a pigment or dye to aid in determining coverage and depth of the applied cement or contrast agents such as barium salts in determining depth on a radiograph.

Other additives can be incorporated into the compositions that enhance the rate of bone formation and/or bone healing rate (osteogenic). These additives comprise a class of osteogenic growth factors including bone morphogenetic proteins (BMP's), such as BMP 7, stem cells, and/or parathyroid hormone (PTH). Other additives such as bisphosphonates can also be contemplated for incorporation into the composition.

Other additives that can be incorporated into the composition are infection preventatives such as broad spectrum antibiotics and anti-infective additives.

While not wishing to be bound by theory, compositions of the present disclosure are believed to function as follows: the multivalent metal compound, which is basic in nature, reacts with the compound that is structurally similar to phosphoserine, which is acidic in nature, upon mixing with the aqueous medium and forms a hardened, layered structure upon curing. This reaction is exothermic; the degree of exothermic activity depends on a number of factors including the volume of the composition. The low pH nature of the compounds that are structurally similar to phosphoserine enable the hydroxyl of phosphate or phosphonate and COOH functional group to bond through ionic interaction with the multivalent metal cations from within the multivalent metal compound. This resulting reactive intermediate continues a cascade of ionic interactions with cations and anions within the multivalent metal compound on the bone surface or any other metal ions of the metal implants. This series of interactions provides transient material having the tacky properties while curing and the adhesion strength that increases upon cure.

The exothermic properties of the composition when curing are prevalent when mixing as a large volume bone void filler (usually greater then 10 cc) and this may serve as an effective means to kill the residual tumor cells locally that remain after surgical bone tumor removal.

The exothermic properties of the composition may lead to necrosis of local tissue and this also reduces the adhesive working time. The amount of heat released by the exothermic reaction is mainly influenced by the volume of the composition, the size of the particles and the ratio of compound that is structurally similar to phosphoserine to the multivalent metal compound. With larger volumes of composition, more heat is released to the surrounding tissue. With volumes less than or equal to 1 cc, the heat release is negligible with maximum temperature reached during the curing of the adhesive being below 40° C. The higher volume compositions greater than 1 cc, may lead to considerable heat release, even exceeding 60° C. in compositions greater than 5 cc. To manage this exothermic heat release to below 45° C., the particle size distribution of the multivalent metal compound, and the ratio of the multivalent metal compound to compound that is structurally similar to phosphoserine can be chosen appropriately. For multivalent metal compounds, it has been found that particles having a mean particle size greater than 15 µm is beneficial. Specifically for TTCP, the smaller particles dissolve and react faster due to a higher specific surface area; therefore, to reduce the exothermic heat release, the composition can be adjusted by choosing a TTCP particle size distribution which generally has a mean particle size greater than 15 µm, more specifically 25 µm. In addition, the greater the amount of multivalent metal compound to the compound that is structurally similar to phosphoserine used, results in a faster reaction due to the number of calcium ions available for bonding. Exothermic heat release can be limited by adding more compound structurally similar to phosphoserine to the composition. To further reduce the exothermic heat release, endothermic additives can be incorporated into the composition to slow the reaction rate; these include polyols (such as sorbitol or mannitol) or PEG. The factors discussed here can be chosen to design several compositions; all of which have exothermic profiles which limit or eliminate necrotic reactions to local tissues while tailoring the compositions with sufficient working time for the clinical application.

The compositions when mixed with aqueous medium typically have a creamy or a tacky paste consistency initially. Also, the mixing of the compositions with the aqueous medium does not require a high level of force or shear and simple hand mixing, such as with a spatula, is sufficient in most instances. It is envisioned that the present compositions may be applied via injection through a syringe or other suitable pressurized implement, applied with a spatula, and as otherwise desirable by a user. The creamy or tacky viscosity allows for application of the composition to the defect site for a defined period of time. The compositions allow the bone to be repositioned several times within 4 minutes and preferably within 2 minutes without losing tacky properties. If the compositions need to be injected through a syringe or cannula, the viscosity of the composition during the working time can be important. For these situations, viscosities of the compositions herein should be preferably below about 150 centipoise.

Still further embodiments have a consistency similar to putty. These embodiments are useful for filling larger defects, have sculpting properties, or for mechanical interlocking into cancellous bone. These compositions hold their cohesive, tacky, and sculpting properties over a longer period of time even when subjected to a wet field. The compositions have working time for sculpting sometimes up to 15 minutes depending on the application requirement, typically up to about 8 minutes, and preferably up to about 5 minutes, after mixing with the aqueous medium. Formulations with an increased amount of compound that is structurally similar to phosphoserine greater than 25% w/w or with an increased multivalent metal compound mean particle size greater than about 250 microns tend to have longer working times and seem to be suitable for use in situations where the putty will fill defects in structures that are well supported by surrounding bone. In these situations the putty does not need to harden as fast provided it maintains its cohesive properties in the wet field. Another property of the compositions is that the compositions will adhere to themselves as well as to an external surface such as bone. This is useful in situations where a shape is formed during the putty state and this shape can then adhere to bone. Also, in some instances a user may apply a mass of the composition to a bone or other surface and then shape the composition into the final desired shape during the working time of the composition.

Compositions which have a putty consistency to be used as a void filler can be enhanced by incorporating macro porous granules or chips to allow for new bone ingrowth. These granules may come from synthetic sources such α-TCP or β-TCP granules or it may be preferred to select the granules or chips from autologous bone sources or demineralized bone to enhance the bone healing rate.

Additional embodiments have a consistency that is thin, free flowing, and paintable. These compositions have an aqueous medium of about 20% to about 30% by weight based on the combined weight of the multivalent metal compound, the compound similar to phosphoserine, and the aqueous medium. The increased amount of aqueous medium does not detract from the adhesive strength in the tacky state. These embodiments are useful for painting or coating on the surface of an implant prior to insertion into a bone structure, which significantly increases the pull out strength of the implant from the bone structure. It is believed that the application of this embodiment on an implant prior to insertion into a bone structure prevents micro motions of the implant shortly after the implant is put in position in the patient and minimizes the implant failure.

It is further envisioned that the cement compositions disclosed herein may be packaged into kits that may include a vial containing the multivalent metal compound with the compound that is structurally similar to phosphoserine prefilled together and packaged under vacuum, nitrogen, or dry air to preserve the shelf life. Further, if additives are used, they may be included within this vial or in a separate vial. The aqueous medium is provided in a separate vial. The kit may include mixing bowls, stirring sticks, spatulas, syringes, and/or any other desirable component for application.

Composition of the current disclosure are envisioned to provide ease of use in different medical applications based on ease of application, duration of use before cure, resistance to in vivo environments, extended maneuverability of bone fragments and/or implant devices prior to cure onset, good load bearing capabilities after cure, and good ultimate bond strength. For example, compositions may have an adequate working period after mixing sometimes up to 15 minutes depending on the application requirement, typically up to about 8 minutes or less, and preferably up to about 5 minutes or less. Further, the relative force of pressure required to inject the composition from an appropriately sized syringe may remain constant or below a certain injection force threshold from the point of mixing and loading the syringe to the end of the working period. It is contemplated that bone fragments adhered together or implanted devices may exhibit moderate separation strengths within the working period. Such moderate separation strengths may be exhibited regardless of the relative compressive force used during apposition. It is further contemplated that cement compositions of the present disclosure may have sufficient material cohesion when applied in moist, wet, greasy and/or fatty saline environments, such as in vivo settings, thereby reducing the need for surface preparation and maintaining a dry environment. As well, good capacity for supporting passive movement and maintaining load and non-load bearing bone fragment alignment after surgery during initial rehabilitation period and active range of motion rehabilitation period are envisioned for cement compositions contemplated herein.

Typical compositions exhibit an adhesive strength upon curing, typically after greater than 10 minutes from initial mixing, in the range of about 250 to about 2,000 kPa on cancellous bone and from about 250 to about 10,000 kPa on cortical bone in at least one of compression, tension, shear, and/or bending. Compositions can be chosen to achieve the strength in these ranges; the level of strength required is dependent upon the clinical application. Also it is important to note that the curing can be either in a wet environment, such as in bodily fluids, or in a dry environment, and the ultimate strength of the bond after cure does not seem to be significantly affected.

In the following examples all shear, tension and bending testing was performed using an Instron® test machine setup as follows. For shear testing, two samples were adhered together using the compositions of the present invention. The samples were either rectangular blocks adhered together along their end faces (90° bond surface), or trapezoidal blocks and each prepared with a 45° face. In the case of the latter, the samples were adhered together along their 45° faces using the compositions of the present invention. One end of the (first) sample was supported and fastened to the machine while the other end was left free and unsupported. The force test probe was placed in a plane normal to the bond line of the composite test specimen (e.g., the two samples adhered together) and force was applied until failure. For tension testing, two samples were adhered using the compositions of the present invention. Each end of the composite test specimen was fixed/clamped and force was applied in tension along the longitudinal axis of the composite test specimen (e.g., 90° to the bond) to pull the specimen apart. Samples were tested until failure. For the 3-point bending testing, each end of the composite test specimen was supported without clamping. The test specimen had a span distance of 35 mm. Force was applied to the top of the sample at the center point (same position as the bond line) until failure. The multivalent metal compounds that were used in all the following examples were commercially available. These materials all contained about 68% to 83% multivalent metal compound.

These compositions as disclosed in this specification can be used for a variety of medical applications. These include the capacity to allow or enhance fracture fixation by adhering both load and non-load bone fragments together alone or in the presence of appropriate immobilization (definitive hardware fixation); capacity to adhere middle ear ossicles and prosthesis together for ossicular chain reconstruction; capacity to enhance screw or bone anchor fixation in low density cancellous bone at and/or after surgery; capacity to allow screw fixation when the core diameter of the screw hole in bone is larger than the screw major diameter; capacity to provide bony contour and/or facial bone augmentation properties; capacity to adhere a metal or bioresorbable plate to fractured bones allowing for reduction and/or elimination of metal or bioresorbable screws used to fix plate to bone; capacity to enhance fixation of a joint replacement prosthesis to bone (e.g. hip acetabular cup or femoral stem), capacity to adhere the junction of at least one of a tendon, ligament, cartilage, a bone graft, and/or a dental implants to bone; capacity to adhere to bony defect perimeters while filling gaps creating a seal to prevent leakage (e.g. cerebral spinal fluid), and capacity to support new bone growth for dental socket or dental ridge augmentation. The compositions may be useful in human use applications and are also useful in veterinary applications. Lastly, the compositions may be useful in similar non-medical applications (e.g. carpentry, construction, under water use) as the compositions will adhere to a wide variety of surfaces including wood, glass, certain plastics, plaster, metals of all types, ceramic materials and the like.

Examples

Phosphate and its Salts Based Formulations

Example 1

Each composition in Table 1 was mixed for 20 seconds in a polycarbonate bowl using either a polycarbonate pestle or spatula. After mixing, the composition was applied using a spatula to both surfaces of bovine cortical bone cubes that had apposing faces. The faces were created with either a 45° angle for the 45° shear/tension test (10×14 mm face) or a 90° angle for isolated shear, tension, or bending tests (9×9.5 mm face). Prior to testing, the bone cubes were incubated within a phosphate buffered saline (PBS) solution bath at 30° C. and had pre-dampened surfaces during composition application. By 90 seconds from the start of mixing, the apposing faces were adhered together and aligned with minimal hand compression force for 10 seconds and were immediately transferred and submerged within a PBS solution bath held at 30° C. for the duration of the cure time. If cured for longer then 10 min, the cubes were incubated at 37° C. After the cure time indicated, the cubes were loaded onto the sample fixtures and tested on an Instron test machine. In the table, n=# is the number of samples tested.

TABLE 1

Adhesive compositions containing TTCP and organic phosphates other than Phosphoserine

| Composition | Adhesion shear strength at 5 min on bovine cortical bones | Adhesion shear strength at 24 hours on bovine cortical bones |
|---|---|---|
| Phosphothreonine 250 mg TTCP 400 mg Water 130 µL | 400 kPa | N/A |
| Tyrosine phosphate 150 mg, TTCP 400 mg Water 270 µL | 890 kPa | N/A |
| Phytic acid sodium salt 150 mg, TTCP 400 mg Water 150 µL | 100 kPa | N/A |
| Phosphoryl aminoethanol 250 mg TTCP 400 mg Water 130 µL | 700 kPa | 420 kPa |
| Phosphoryl aminoethanol 250 mg Citric acid 50 mg TTCP 400 mg Water 170 µL | 540 kPa | 460 kPa |
| Methylene Diphosphonic acid 185 mg TTCP 400 mg Beta-TCP granµLes Water 360 µL | 130 kPa | N/A |

Example 2

The compositions of Table 2 were prepared and tested in the same manner as in Example 1. All testing was on bovine cortical bone. All testing was conducted at 5 minutes cure unless otherwise indicated. All testing was 90° shear testing unless otherwise indicated.

TABLE 2

Adhesive compositions containing derivitized Phosphoserine and TTCP

| Composition | Adhesion strength at 5 min on bovine cortical bones | Adhesion strength at 24 hours on bovine cortical bones |
|---|---|---|
| Phosphoserine Mono Sodium salt 250 mg TTCP 400 mg Water 130 µL | 120 kPa | N/A |
| Phosphoserine DiSodium salt 250 mg $CaCl_2$ 100 mg Water 180 µL | 300 kPa | N/A |
| Phosphoserine Trisodium salt 250 mg $CaCl_2$ 165 mg Water 165 µL | 80 kPa | N/A |
| Phosphoserine-ethyleneglycol-diglycidyl-phophoserine 250 mg TTCP 400 mg Water 130 µL | 3.76 MPa | N/A |
| Phosphoserine-citric acid conjugate 10 mg $CaCl_2$ (10% Solution) 10 µL | Forms sticky mass (not cored enough to test) | N/A |
| Phosphoserine-succinic acid dimer 250 mg TTCP 400 mg Water 140 µL | 272 kPa | N/A |

Example 3

The compositions of Table 3 were prepared and tested in the same manner as in Example 1. All testing was on cortical bovine bone. All testing was conducted at 5 minutes cure. All testing was 45° shear/tension.

TABLE 3

Adhesive compositions containing Phosphoserine and Calcium Phosphates other than TTCP

| Composition | Adhesion strength at 5 min on bovine cortical bones | Adhesion strength at 24 hours on bovine cortical bones |
|---|---|---|
| CaO 200 mg MonoCalcium Phosphate Monohydrate 600 mg Phosphoserine 500 mg Water 260 µL | 820 kPa (n = 3) | N/A |
| CaO 100 mg MonoCalcium Phosphate Monohydrate 700 mg Phosphoserine 500 mg Water 330 µL | 10 kPa (n = 3) | N/A |
| CaO 100 mg Dicalcium Phosphate anhydrous 700 mg Phosphoserine 500 mg Water 350 µL | 170 kPa (n = 3) | N/A |

TABLE 3-continued

Adhesive compositions containing Phosphoserine
and Calcium Phosphates other than TTCP

| Composition | Adhesion strength at 5 min on bovine cortical bones | Adhesion strength at 24 hours on bovine cortical bones |
|---|---|---|
| Alpha-TCP (ground flakes) 400 mg Phosphoserine 250 mg Water 133 µL | 640 kPa | 2.88 MPa |

Example 4

The compositions of Table 4 were prepared and tested in the same manner as in Example 1. All testing was on cortical bovine bone. All testing was conducted at 5 minutes cure. All testing was 45° shear/tension.

TABLE 4

Adhesive formulations containing
Strontium salts and Phosphoserine

| Composition | Adhesion strength at 5 min on bovine cortical bones | Adhesion strength at 24 hours on bovine cortical bones |
|---|---|---|
| Strontium Oxide 800 mg Phosphoserine 500 mg Glycerol 1.5 mL | 20 kPa (n = 3) | N/A |
| Strontium Oxide 300 mg Phosphoserine 500 mg MonoCalcium Phosphate Monohydrate 300 mg Water 300 µL | 35 kPa (n = 3) | N/A |
| Dicalcium Phosphate anhydrous 300 mg Strontium Oxide 300 mg Phosphoserine 500 mg Water 300 µL | 100 kPa (n = 3) | N/A |
| Strontium Acetate 800 mg Phosphoserine 500 mg Water 1000 µL | 430 kPa (n = 3) | N/A |
| Strontium Acetylacetone 800 mg Phosphoserine 500 mg Water 500 µL | 50 kPa (n = 3) | |

Example 5

The compositions of Table 5 were prepared and tested in the same manner as in Example 1. Samples 1-6 comprise 1200 mg of TTCP, 900 mg of phosphoserine, and 720 mL of water (approximately 25.5% by weight based on the combined weight of TTCP, phosphoserine, and water). All testing was on cortical bovine bone and was 45° shear/tension. The compositions of Samples 1-6 are a thin, free flowing and paintable tacky material, in contrast to the thick, viscous, and tacky material of Examples 1-4, and are suitable to paint on the keel surface of a Co—Cr #6 knee implant prior to insertion of the implant into the knee. The formulations simificantly increase the base plate pull out strength from the bovine knee as shown in Table 5.

TABLE 5

Bovine Knee Metal Implant Synthetic Adhesive

| Sample | Control pull out strength | Adhesive dose; type of application | Cure time at 37 C. in water | Pull out strength after cure | Net increase in pull out strength by adhesive | Percentage increase of pull out strength | Comments |
|---|---|---|---|---|---|---|---|
| 1 | 289 N | 10X dose; painted the keel surface with brush | 12 hr | 559 N | 270 N | 93% | Formulation mix time 20 sec; immediately painted the keel surface for up to 1 min, inserted the keel into the knee at 1 min 45 sec |
| 2 | 0 (sample knee has a large void, porous bone) | 40X dose; painted the keel surface with brush and the remaining material poured into the void (60% void filled with material) | 3 hr | 256 N | 256 N | 256% | Filling the void with adhesive enhanced the strength |

TABLE 5-continued

Bovine Knee Metal Implant Synthetic Adhesive

| Sample | Control pull out strength | Adhesive dose; type of application | Cure time at 37 C. in water | Pull out strength after cure | Net increase in pull out strength by adhesive | Percentage increase of pull out strength | Comments |
|---|---|---|---|---|---|---|---|
| 3 | 405 N | 3X dose; painted the keel surface with brush | 3 hr | 638 N | 233 N | 58% | For a healthy knee, even a low dose formulation works well |
| 4 | 0 (very porous bone, has void) | 10X dose; painted the keel surface with brush; the 30% void was filled with the remaining adhesive material | 2 hr | 487 N | 487 N | 487% | Void filling might help in gaining strength |
| 5 | 297 N | 10X dose; painted the keel surface with brush; | 1 hr | 508 N | 211 N | 71% | |
| 6 | 289 N | 10X dose; painted the keel surface with brush | 12 hr | 559 N | 270 N | 93% | Formulation mix time 20 sec; immediately painted the keel surface for up to 1 min, inserted the keel into the knee at 1 min 45 sec |

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

What we claim is:

1. An adhesive composition comprising:
a multivalent metal compound; and
a compound of the formula:

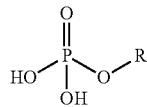

wherein R is one of Groups I, II, III, IV, V, VI, or VII:

Group I:

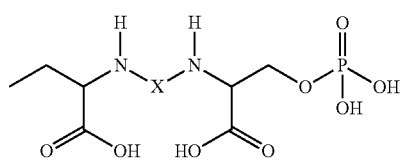

wherein X is selected from the group consisting of Groups Ia, Ib, Ic, Id, and Ie:

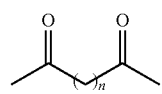

Group Ia

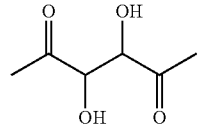

Group Ib

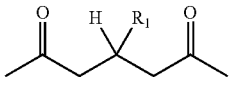

Group Ic

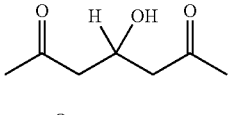

Group Id

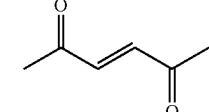

Group Ie where n is an integer from 0 to 6, and $R_1$ is a carboxylic acid group, a sodium carboxylic acid salt or Group If:

Group If:

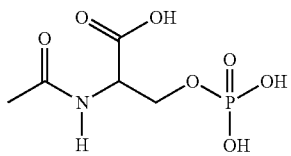

Group II:

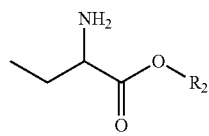

where $R_2$ is selected from the group consisting of Groups IIa, IIb, IIc, IId, IIe, and IIf, a pyridoxyl group, a nicotinic acid group, a salicylic acid group, and a tyrosine group;

Group IIa:

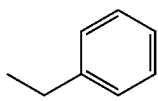

Group IIb:

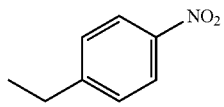

Group IIc:

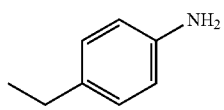

Group IId:

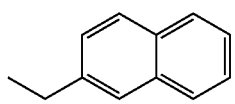

Group IIe:

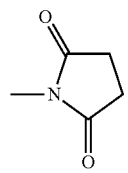

Group IIf:

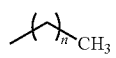

where n is an integer from 1 to 11;

Group III:

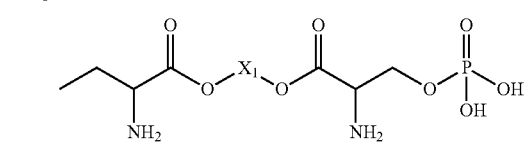

wherein $X_1$ is a linking group selected from the group consisting of C1 to C12 aliphatic diols, aromatic diols, Group IIIa, sugar, monosaccharides, and disaccharides;

Group IIIa:

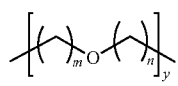

wherein m and n are each integers from 1 to 2 and y is a number from 1 to 100;

Group IV:

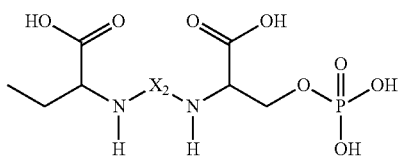

wherein the compound comprises a phosphoserine oligomer or a phosphoserine capped polymer of Group IV having from 2 to 10 repeating groups, and wherein $X_2$ is selected from one or more amino acids of Groups IVa, IVb, or IVc, polyesters selected from homopolymers and copolymers of caprolactone, lactide, glycolide, hydroxybutyrate, ethylene glycol linked phosphoserine, and mixtures thereof;

Group IVa:

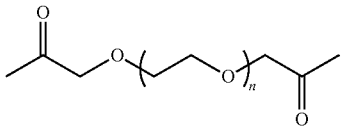

Group IVb:

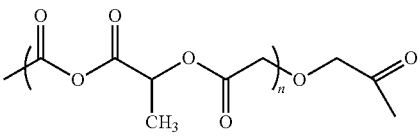

Group IVc:

wherein n is a number from 1 to 50, wherein the polylactic glycolic acid (PLGA) of Group IVb has a ratio of lactic acid to glycolic acid being from about 0:100 to about 100:0, more preferably from about 30:70 to about 50:50, and the PLGA may be linear, hyperbranched, or star shaped;

Group V:

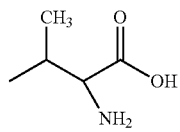

wherein the compound exists in one of the L, D, and racemic forms;

Group VI:

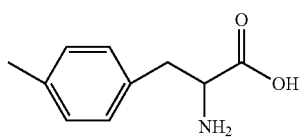

wherein the compound exists in one of the L, D, and racemic forms;

Group VII:

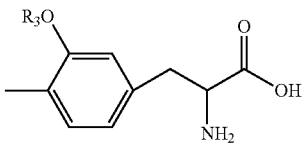

wherein $R_3$ is H or —P(O)(OH)$_2$, and wherein the compound exists in one of the L, D, and racemic forms;
wherein the compound is present in an amount from about 10% to about 90% by weight based on the combined weight of the multivalent metal compound and the compound; and
an aqueous medium in an amount of up to about 35% by weight based on the combined weight of the multivalent metal compound, the compound, and the aqueous medium.

2. The composition of claim 1 wherein the multivalent metal compound is selected from the cation group consisting of calcium, magnesium, barium, strontium, iron, zinc, titanium, zirconium, and mixtures thereof.

3. The composition of claim 2 wherein the multivalent metal compound is selected from the group consisting of tetracalcium phosphate, tricalcium phosphate, tristrontium phosphate, and tetrastrontium phosphate.

4. The composition of claim 1 wherein the multivalent metal compound is selected from the anion group consisting of phosphates, oxides, carbonates, bicarbonates, sulfates, hydroxides, chlorides, acetates, fatty acid salts, acetylacetones, nitrates, and mixtures thereof.

5. The composition of claim 1 wherein the multivalent metal compound is crystalline, amorphous, or mixtures thereof.

6. The composition of claim 1 wherein the compound is present in an amount from about 15% to about 50% by weight based on the combined weight of the multivalent metal compound and the compound.

7. The composition of claim 1 wherein the aqueous medium is present in an amount from about 14% to about 19% by weight of the total composition.

8. The composition of claim 1 wherein the compound is selected from the group consisting of tyrosine phosphate, threonine phosphate, 3,4-dihydroxyphenylalanine (DOPA) monophosphate, DOPA diphosphate, and mixtures thereof.

9. The composition of claim 1 wherein the compound is phosphoserine, tyrosine phosphate, theronine phosphate, DOPA monophosphate, and DOPA diphosphate.

10. The composition of claim 1 wherein the multivalent metal compound has a mean particle size of less than 1000 microns.

11. The composition of claim 1 wherein the aqueous medium is water.

12. The composition of claim 1 wherein the aqueous medium is a blood based product.

13. The composition of claim 1 that further includes an additive.

14. The composition of claim 13 wherein the additive is selected from the group consisting of alpha tri-calcium phosphate, beta tri-calcium phosphate, calcium sulfate, calcium silicate, calcium carbonate, sodium bicarbonate, sodium chloride, potassium chloride, glycerol phosphate disodium, amino acids, polyols, trehalose, lactose, sucrose, silk, keratin, autologous bone powder or chips, demineralized bone powder, demineralized bone chips, collagen, biodegradable polymers, bone morphogenetic protein 7, stem cells, parathyroid hormone, bisphosphonates, and mixtures thereof.

15. The composition of claim 13 wherein the additive is a reaction rate modifier.

16. The composition of claim 13 wherein the additive is a pore former.

17. The composition of claim 13 wherein the additive enhances resorption.

18. The composition of claim 13 wherein the additive is a strength modifier.

19. The composition of claim 13 wherein the additive promotes bone healing.

20. The composition of claim 13 wherein the additive is a contrast agent.

21. The composition of claim 1 wherein the composition has a tacky state for up to about 12 minutes after mixing with the aqueous medium.

22. The composition of claim 21 wherein the composition during the tacky state has a separation strength in the range of about 10 kPa to about 250 kPa after mixing with the aqueous medium.

23. The composition of claim 1 wherein the composition has a putty state for up to about 15 minutes after mixing with the aqueous medium.

24. The composition of claim 1 wherein the composition has a working time for up to about 26 minutes after mixing with the aqueous medium.

25. The composition of claim 1 wherein the composition has an adhesive strength upon curing of greater than 250 kPa.

26. The composition of claim 25 wherein the adhesive strength is for bone to a non-bone material.

27. The composition of claim 25 wherein the adhesive strength is for bone to bone.

28. The composition of claim 25 wherein the adhesive strength is for non-bone material to non-bone material.

29. The composition of claim 1 wherein the composition is resorbable by the body.

30. The composition of claim 1 wherein the compound is present in an amount from about 20% to about 40% by weight based on the combined weight of the multivalent metal compound and the compound.

31. The composition of claim 1 wherein the composition has a tacky state for up to about 4 minutes after mixing with the aqueous medium.

32. The composition of claim 1 wherein the composition has a tacky state for up to about 2 minutes after mixing with the aqueous medium.

33. The composition of claim 21 wherein the composition during the tacky state has a separation strength in the range of about 50 kPa to about 150 kPa after mixing with the aqueous medium.

34. The composition of claim 1 wherein the composition has a putty state for up to about 8 minutes after mixing with the aqueous medium.

35. The composition of claim 1 wherein the composition has a putty state for up to about 5 minutes after mixing with the aqueous medium.

36. The composition of claim 1 wherein the composition has a working time for up to about 12 minutes after mixing with the aqueous medium.

37. The composition of claim 1 wherein the composition has a working time for up to about 7 minutes after mixing with the aqueous medium.

* * * * *